(12) United States Patent
Kelley

(10) Patent No.: US 6,524,302 B2
(45) Date of Patent: Feb. 25, 2003

(54) MULTI-LUMEN CATHETER

(75) Inventor: Gregory S. Kelley, San Diego, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/843,420

(22) Filed: Apr. 26, 2001

(65) Prior Publication Data

US 2002/0161327 A1 Oct. 31, 2002

(51) Int. Cl.[7] .............................................. A61M 25/00
(52) U.S. Cl. ........................ 604/523; 604/524; 604/525
(58) Field of Search ................................ 604/165, 173, 604/264, 523, 524, 525, 96.01

(56) References Cited

U.S. PATENT DOCUMENTS

| | | |
|---|---|---|
| 399,985 A | 3/1889 | Goodwillie |
| 1,696,018 A | 12/1928 | Schellberg |
| 2,173,527 A | 9/1939 | Agayoff |
| 2,561,569 A | 7/1951 | Flynn |
| 3,064,653 A | 11/1962 | Coanda |
| 3,174,890 A | 3/1965 | Goyki |
| 3,322,590 A | 5/1967 | Clark |
| 3,467,180 A | 9/1969 | Pensotti |
| 3,469,579 A | 9/1969 | Hubert |
| 3,625,793 A | 12/1971 | Sheridan |
| 3,720,210 A | 3/1973 | Diettrich |
| 3,817,389 A | 6/1974 | Weichselbaum |
| 3,976,529 A | 8/1976 | Weichselbaum |
| 4,003,665 A | 1/1977 | Dreyer |
| 4,050,667 A | 9/1977 | Kossett |
| 4,063,980 A | 12/1977 | Trunnell |
| 4,838,881 A | 6/1989 | Bennett |
| 5,042,985 A | 8/1991 | Elliott |
| 5,295,962 A | 3/1994 | Crocker |
| 5,300,099 A | * 4/1994 | Rudie .......................... 604/20 |
| 5,322,508 A | 6/1994 | Viera |
| 5,342,301 A | * 8/1994 | Saab ...................... 604/103.13 |
| 5,569,184 A | * 10/1996 | Crocker et al. ......... 604/103.01 |
| 5,571,086 A | 11/1996 | Kaplan |
| 6,102,904 A | 8/2000 | Vigil |
| 6,306,074 B1 | * 10/2001 | Waksman et al. ............... 600/7 |

* cited by examiner

Primary Examiner—Lesley D. Morris
Assistant Examiner—John Fristoe
(74) Attorney, Agent, or Firm—Kenyon & Kenyon

(57) ABSTRACT

A multi-lumen catheter and method of manufacturing such a multi-lumen catheter having a plurality of individual catheter tubes. Each catheter tube has an outer surface, an inner surface and a lumen. The catheter tubes can be made of different thermoplastic materials. A mandrel is first inserted into the lumen of each catheter tube to provide support. The catheter tubes are then juxtaposed to each other in an arrangement. Importantly, the outer surface of one catheter tube is in contact with the outer surface of at least one other catheter tube in the arrangement. The arrangement of catheter tubes is then held in a sleeve and is advanced through the sleeve, and through a heating cylinder to fuse the outer surfaces of the catheter tubes. A cooling means is placed in the lumen of each catheter tube to prevent the inner surface of each catheter tube from melting.

12 Claims, 2 Drawing Sheets

MULTI-LUMEN CATHETER

FIELD OF THE INVENTION

The present invention pertains generally to catheters and methods for the manufacture of catheters. More particularly, the present invention pertains to multi-lumen catheters that are made from a plurality of individual tubes. The present invention pertains particularly, though not exclusively, to multi-lumen catheters having low profiles.

BACKGROUND OF THE INVENTION

There are numerous health care situations wherein a multi-lumen catheter is useful in the treatment of a patient. For instance, it may be necessary for a patient to receive several different medications at the same time. A multi-lumen catheter can simultaneously infuse a plurality of medications into a patient and, if necessary or desirable, the separate lumens of the multi-lumen catheter can prevent the medications from interacting with each other during the infusion process into the patient. Another example where a multi-lumen catheter may be useful is when it is necessary to infuse medication into a patient's body while simultaneously withdrawing bodily fluid samples such as blood from the patient.

For several reasons, whenever interventional procedures are required, it is most often desirable to perform the necessary treatment on the patient through a single puncture site. The use of a multi-lumen catheter obviously eliminates the need for numerous punctures in a patient and thus minimizes patient discomfort.

Several types of multi-lumen catheters are well known. For example, U.S. Pat. No. 5,167,623 which issued to Cianci, et al. for an invention entitled "Multilumen Catheter" discloses a multi-lumen catheter having a flexible first tube and a flexible dual-lumen tube which is disposed in the first tube. Another example of a multi-lumen catheter is U.S. Pat. No. 4,072,146 which issued to Howes for an invention entitled "Venous Catheter Device." This patent discloses three independent non-coaxial circular tubes placed in a larger tube. Yet another example is a multi-lumen catheter having a unitary catheter tube with a septum forming two large, roughly elliptically shaped lumens and a small infusion lumen extending along the interior wall of the unitary tube. Such a multi-lumen catheter is disclosed in U.S. Pat. No. 5,221,256 which issued to Mahurkar for an invention entitled "Multiple-Lumen Catheter."

Despite the fact there are many multi-lumen catheters in the pertinent art, there still exist several common problems associated with these types of catheters. For example, a typical problem concerning a multi-lumen catheter is its size. In order to minimize trauma to the patient, however, it is desirable to make the smallest possible puncture in a patient's body. Consequently, a catheter should have the smallest possible cross-sectional area. Some multilumen catheters, however, use additional material to hold the plurality of tubes together which can really increase the cross-sectional area. An example of this is the multi-lumen catheter mentioned above which is disclosed in U.S. Pat. No. 4,072,146 having three independent non-coaxial tubes disposed in a larger tube. The cross-sectional area of this particular multi-lumen catheter is relatively large because of the additional large tube that is used to hold the three tubes together.

In addition to problems with large cross-section areas, multi-lumen catheters can also have problems regarding steerability and pushability. For instance, a catheter must be flexible in order for the catheter to be steered and maneuvered through the convoluted and narrow passageways of the body. At the same time, however, the catheter must also be sufficiently stiff for the catheter to be pushed into the passageway to reach a site that is at a considerable distance from the point of entry of the catheter into the patient's body. The problems with steerability and pushability derive from the material with which the multi-lumen catheter is made. The crux of the problem is that a material usually possesses one good characteristic at the expense of other characteristics. Therefore, multi-lumen catheters that are made of only one material may not sufficiently accomplish all the functional requirements.

In light of the above, it is an object of the present invention to provide a multi-lumen catheter having a low profile and a method for manufacturing such a catheter. Another object of the present invention is to provide a multilumen catheter having a plurality of independent catheter tubes that are fused together to reduce their cross-sectional profile. Yet another object of the present invention is to provide a multi-lumen catheter having catheter tubes that can be made from different thermoplastic materials and having varying lengths to provide for operational requirements. Still another object of the present invention is to provide a multi-lumen catheter which is relatively simple to manufacture, easy to use, and comparatively cost effective.

SUMMARY OF THE PREFERRED EMBODIMENTS

The present invention is directed to a multi-lumen catheter and a method for manufacturing such a catheter. For the present invention, the multi-lumen catheter includes a plurality of individual catheter tubes, each having an outer surface, an inner surface, and a lumen. As intended for the present invention, the plurality of catheter tubes may have varying lengths as well as varying diameters. Importantly, each catheter tube can be made of a selected thermoplastic material, and the various tubes can be made of different materials. Of equal importance, the catheter tubes can also be made of the same thermoplastic material, if so desired.

In the manufacture of the present invention, a mandrel is first inserted into the lumen of each catheter tube to provide support to the catheter tubes. Next, the plurality of catheter tubes are juxtaposed with each other in a coextended desired arrangement. It is important for the outer surface of one catheter tube to be in contact with the outer surface of at least one other catheter tube in the arrangement. The arrangement of the catheter tubes is then disposed in a sleeve which holds the catheter tubes in place and prevents them from crossing or tangling with each other.

In fusing the catheter tubes to each other, the arrangement of catheter tubes is first placed in front of a heating cylinder. The plurality of catheter tubes in the sleeve are then simultaneously advanced through the sleeve, and through the heating cylinder. As the catheter tubes are advanced through the heating cylinder, the outer surfaces of the catheter tubes are fused together where their outer surfaces are in contact with each other. As a result, there is a change in structure as the outer surfaces of the individual catheter tubes become a contiguous outer surface for the fused catheter tubes.

In any case, the sleeve continues to hold the remaining lengths of the catheter tubes in place as they are advanced into the heating cylinder. The sleeve itself, however, does not enter the heating cylinder. In this manner, the plurality of catheter tubes of the present invention continue to be advanced through the heating cylinder until the entire lengths of the catheter tubes are fused.

As stated above, each catheter tube can be made of a different thermoplastic material. It is necessary, however, for each thermoplastic material to be miscible with each other. Stated another way, the melting point temperatures of the thermoplastic materials are in a close range of each other. This is important because the outer surface of each catheter tube must melt as it is advanced through the heating cylinder.

It is important to note that the method of the present invention for fusing the catheter tubes together is dependent upon the temperature that is used for fusing, the time the materials are exposed to the heat and the volume and surface contact area of the materials that are being fused. Insofar as temperature is concerned, the heating cylinder is operated at a substantially constant temperature that is greater than the lowest melting point temperature of the thermoplastic materials that are being used for the catheter tubes. Further, the rate at which the catheter tubes pass through the heating cylinder will vary depending upon the size of the catheter tubes and the number of catheter tubes that are to be fused together. For example, the rate at which two catheter tubes pass through the heating cylinder will most likely be faster than the rate for three catheter tubes because two catheter tubes will fuse faster than three catheter tubes. In any case, the purpose here is to have the outer surfaces of the catheter tubes melt uniformly as the heating cylinder radiates heat on the arrangement of the catheter tubes.

Importantly, only the outer surfaces of the catheter tubes are melted during the manufacture of a multi-lumen catheter. Unlike the outer surfaces of the catheter tubes that are heated and fused to each other, the temperature of the material at the inner surfaces of the catheter tubes needs to be held below the melting point in order to maintain the structural integrity of the catheter tubes. In order to prevent the inner surfaces of the catheter tubes from melting, the inside surface of each catheter tube needs to be cooled. This can be done by the mandrel, which generally acts as a sufficient heat sink. Alternatively, air or water can be blown through each mandrel in each catheter tube to prevent the inner surface of the catheter tube from melting. For the present invention, the mandrel is preferably a stainless steel hypo tube.

As also contemplated in the manufacture of the multi-lumen catheter of the present invention, in order to properly perform a specific function, a catheter tube can include an inner liner which may be of a material that is suitable for the purpose. For example, a particular liner may be preferred for infiltrating radiopharmaceuticals through the catheter tube. In this case, the inner liner is preferably made of polyethylene. The catheter tube itself, however, may be immiscible with its liner. For example, when the tube is made of polybutylene terephthalate polyether glycol, which is sold under the trademark HYTREL®, the polyethylene inner liner of the catheter tube may not fuse with the polybutylene terephthalate polyether glycol material of the other catheter tube. In this case, a tie layer may need to be used to bond the inner liner with the thermoplastic material of the catheter tube. A tie layer suitable for this example is preferably made of a polyolefin adhesive, such as the material sold under the trademark PLEXAR PX380®.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
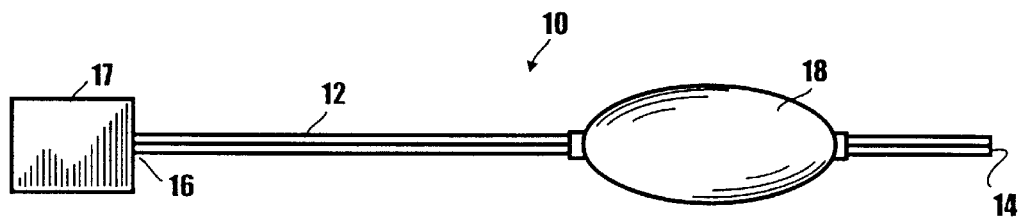
FIG. 1 is a perspective view of the multi-lumen catheter of the present invention with a balloon attached thereto.

Referring initially to FIG. 1, a multi-lumen catheter in accordance with this present invention is shown and is generally designated 10. As shown, the multi-lumen catheter 10 has a tubular member 12 having a distal end 14 and a proximal end 16. Although there are several applications for using the multilumen catheter 10 of the present invention, only one application, as an example, is shown in the drawings. Such an application is shown in FIG. 1 where a fluid source 17 is attached to the proximal end 16 of the tubular member 12 and a balloon 18 is attached near the distal end 14 of the tubular member 12. For this application of the present invention, balloon 18 is preferably made of any suitable angioplasty balloon material, such as polyethylene terephthalate or polyurethane.

Figure 2:
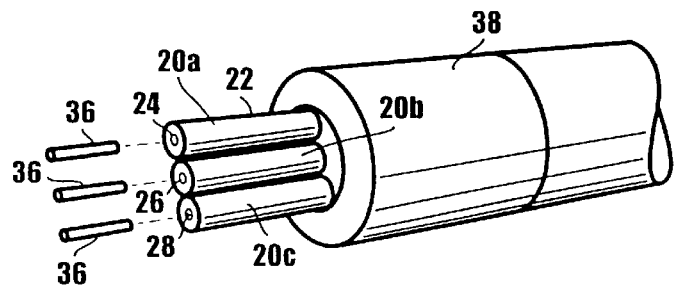
FIG. 2 is a schematic exploded view showing mandrels positioned for insertion into the catheter tubes that are being held in a sleeve.

Regardless of the particular application for the present invention, the tubular member 12 of the multi-lumen catheter 10 includes a plurality of individual catheter tubes 20 as shown in FIG. 2. Although FIG. 2 shows three catheter tubes 20a-c of the present invention, this is only exemplary, as there may be more or fewer catheter tubes 20 depending on the particular need.

Figure 5:
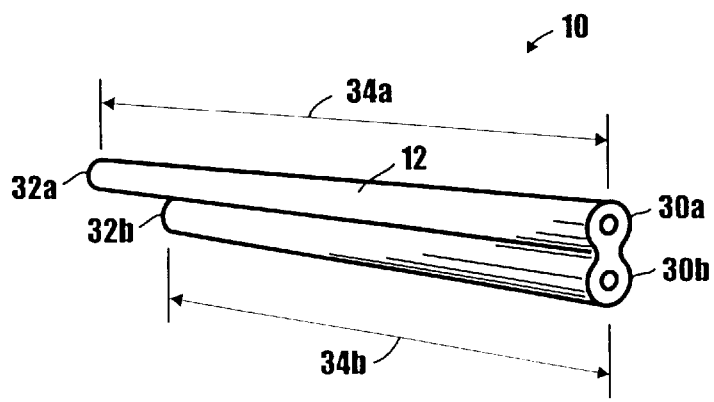
FIG. 5 is a perspective view of an alternate embodiment of the present invention.

In any case, each catheter tube 20 has an outer surface 22, an inner surface 24, and a lumen 26 with a diameter 28. The catheter tubes 20 of the present invention are shown to have substantially the same size diameters 28. This is only exemplary as the diameter size and thickness of each catheter tube 20 can vary. Each catheter tube 20 also has a distal end 30, a proximal end 32, and a length 34 which can be clearly seen in FIG. 5. It can also be seen in FIG. 5 that the catheter tubes 20a and 20b of the present invention can also have varying lengths 34a and 34b. As intended for the present invention, each catheter tube 20 can be made of a selected thermoplastic material. Importantly, the catheter tubes 20 can be made of different materials.

In the manufacture of the multi-lumen catheter 10 of the present invention, a mandrel 36 is first inserted into the lumen 26 of each catheter tube 20 as shown in FIG. 2. Each mandrel 36 provides support for its respective catheter tube 20. The plurality of catheter tubes 20 are juxtaposed with each other in a coextended desired arrangement. It is important for the outer surfaces 22 of the catheter tubes 20 to be in contact with each other in the arrangement. Stated another way, the outer surface 22 of one catheter tube 20 is in contact with the outer surface 22 of at least one other catheter tube 20. As also shown in FIG. 2, the arrangement of catheter tubes 20 is placed in a sleeve 38 which holds the plurality of catheter tubes 20 in place to prevent them from crossing or tangling with each other.

Figure 3:
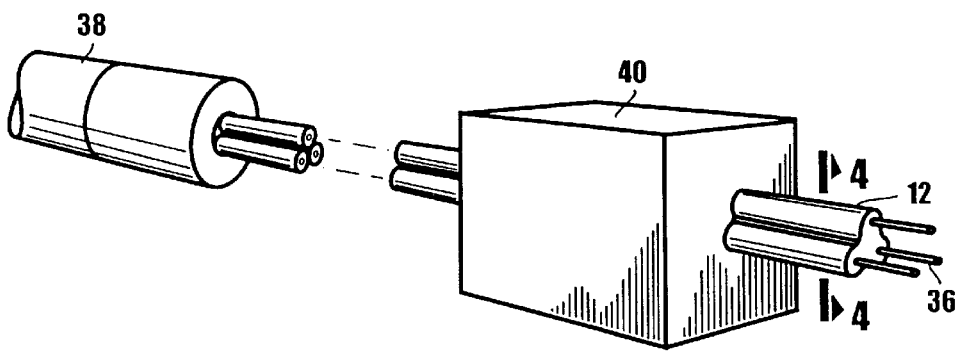
FIG. 3 is a schematic drawing of a catheter being advanced through a heating cylinder of the present invention.
Figure 4:
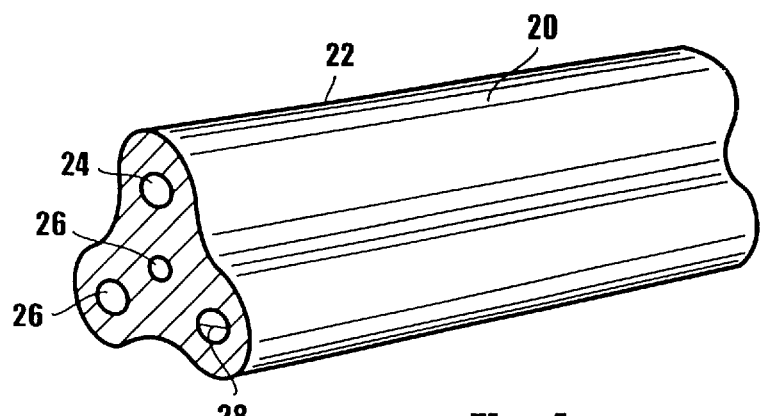
FIG. 4 is a cross-sectional view of the multi-lumen catheter of the present invention as seen along line 4—4 in FIG. 3.

In fusing the catheter tubes 20 to each other, the arrangement of catheter tubes 20, held by sleeve 38, is placed in front of a heating cylinder 40 as shown in FIG. 3. The sleeve 38 will remain outside the heating cylinder 40 as the plurality of catheter tubes 20 are simultaneously advanced through the sleeve 38, and through the heating cylinder 40. As the catheter tubes 20 are advanced through the heating cylinder 40, the outer surfaces 22 of the catheter tubes 20 are fused together where their outer surfaces 22 are in contact with each other. As a result, there is a change in structure as the outer surfaces 22 of the individual catheter tubes 20 become a contiguous outer surface 22 for the fused catheter tubes 20 as shown in FIG. 4. In any case, the sleeve 38 continues to hold the remaining lengths 34 of the catheter tubes 20 in place as they are advanced into the heating cylinder 40 until the entire lengths 34 of the catheter tubes 20 are fused together.

As contemplated, the method of the present invention for fusing a plurality of catheter tubes is dependent upon time, temperature and volume. For the temperature requirement, it is necessary for the heating cylinder 40 to be operated at a substantially constant temperature that is greater than the lowest melting point temperature of the thermoplastic materials of the catheter tubes 20. Importantly, the thermoplastic material for each catheter tube 20 must be miscible with each other in order for the thermoplastic materials to melt at one temperature. Further, the rate at which the catheter tubes 20 pass through the heating cylinder 40 in order for the outer surfaces 22 of the catheter tubes 20 to melt uniformly will depend upon the number of catheter tubes 20 that are to be fused together.

As shown in FIG. 4, and as mentioned above, there is a structural change in the outer surface 22 for the fused catheter tubes 20. As also shown in FIG. 4, an additional lumen 26 is created from the outer surfaces 22 of the three fused catheter tubes 20. This is only exemplary for the results of the fused catheter tubes 20 can vary depending upon parameters of each catheter tube 20 selected and the number of catheter tubes 20 fused together.

Figure 6:
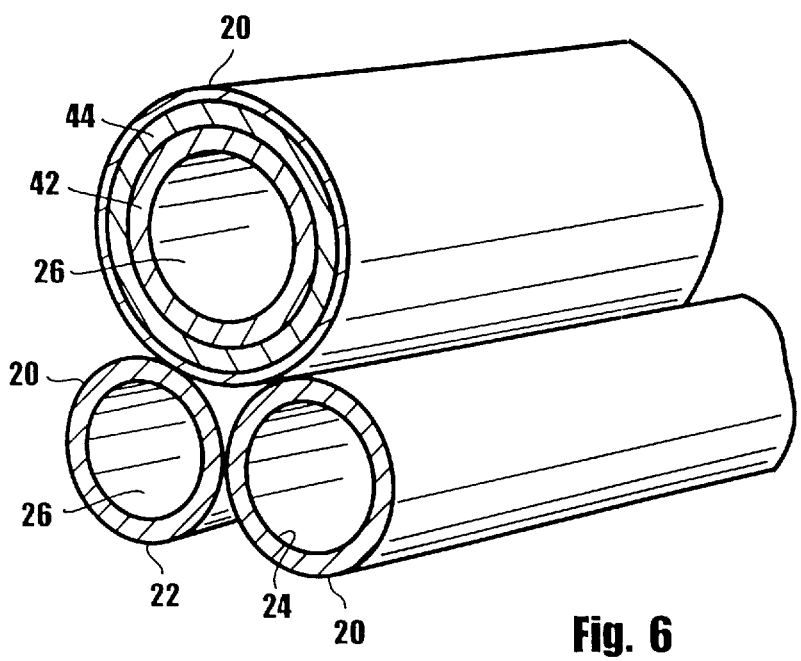
FIG. 6 is a cross-sectional view of an alternate embodiment of the present invention as would be seen along the line 6—6 in FIG. 3 prior to being advanced through the heating cylinder.

Unlike the outer surfaces 22 of the catheter tubes 20 that are fused to each other, it is important that the inner surfaces 24 of the catheter tubes 20 keep the structural integrity of the catheter tubes 20. In order to do this, a cooling means can be placed inside each catheter tube 20 prior to melting the outer surfaces 22 of the catheter tubes 20. Preferably, the cooling means is the mandrel 36, which generally acts as a sufficient heat sink. Alternatively, the mandrel is preferably a stainless steel hypo tube. If a hypo tube is used, air or water can be blown through each mandrel of each catheter tube 20 to cool the tube 20 and prevent the inner surface 24 of the catheter tube 20 from melting. FIG. 6 shows an alternative embodiment of the present invention with one catheter tube 20 having an inner liner 42. This is only exemplary, as there may be more catheter tubes 20 having inner liner 42 depending on the particular need. For example, the inner liner 42 of the present invention may be made of polyethylene. A polyethelene inner liner 42, however, may be immiscible with the thermoplastic material of the catheter tube 20, which is preferably polybutylene terephthalate polyether glycol, such as the material sold under the trademark HYTREL®. Thus, the polyethylene inner liner 42 of the catheter tube 20 may not fuse with the polybutylene terephthalate polyether glycol material of the catheter tubes 20. If so, a tie layer 44, as shown in FIG. 6, is used to connect the inner liner 42 with the inner surface 24 of the catheter tube 20. Importantly, this tie layer 44 is preferably made of a polyolefin adhesive, such as the material sold under the trademark PLEXAR PX380®.

With the above description of the present invention in mind, it should be noted that there are several variables bearing on the manufacture of the multi-lumen catheter 10 of the present invention. As mentioned above, each catheter tube 20 can be made of a different thermoplastic material as long as each thermoplastic material is miscible with at least one other thermoplastic material. Secondly, the thickness of each catheter tube 20 used in the manufacture of a multi-lumen catheter 10 can also vary. Thus, because of the varying thickness of each catheter tube 20, the speed at which the catheter tubes 20 are advanced through the heating cylinder 40 will also vary in order for the catheter tubes 20 to melt uniformly. Finally, in order to prevent the inner surfaces 24 of the catheter tubes 20 from melting, the cooling temperature inside the lumen 26 of each catheter tube 20 will also vary depending upon the temperature of the heating cylinder 40.

While the particular Multi-Lumen Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A multi-lumen catheter which comprises:

a first tube having an outer surface;

a second tube having an outer surface;

a third tube having an outer surface;

a first fused area of melted and fused thermoplastic material at a region where said outer surface of said first tube is fused to said outer surface of said second tube; and a second fused area of melted and fused thermoplastic material at a region where said outer surface of said second tube is fused to said outer surface of said third tube;

whereby the fusing together of said tubes integrates said first tube with said second tube and said second tube with said third tube; and wherein a cross-section of the multi-lumen catheter has an outer periphery with at least three distinct lobes, with each distinct lobe corresponding to one of said fused tubes.

2. A multi-lumen catheter as recited in claim 1 further comprises a balloon mounted on said multi-lumen catheter, said balloon in fluid communication with at least one said tube.

3. A multi-lumen catheter as recited in claim 1 wherein each said tube has a length wherein said length of one said tube is different from said length of at least one other said tube and further wherein said tubes have diameters that are substantially the same size.

4. A multi-lumen catheter as recited in claim 1 wherein said first tube has an inner liner, said inner liner being bonded to said first tube with a tie layer.

5. A multi-lumen catheter as recited in claim 1 wherein each said tube is made of a thermoplastic material and wherein said thermoplastic material of one said tube is the same said thermoplastic material of at least one other said tube.

6. A multi-lumen catheter as recited in claim 5 wherein each said thermoplastic material is miscible with each other.

7. A multi-lumen catheter which comprises:
- a first tube having an outer surface;
- a second tube having an outer surface;
- a first fused area of melted and fused thermoplastic material at a region where said outer surface of said first tube is fused to said outer surface of said second tube;
- whereby the fusing together of said tubes integrates said first tube with said second tube; and
- wherein a cross-section of the multi-lumen catheter has an outer periphery with at least two distinct lobes, with each distinct lobe corresponding to one of said fused tubes.

8. A multi-lumen catheter as recited in claim 7 further comprising a balloon mounted on said multi-lumen catheter, said balloon in fluid communication with at least one said tube.

9. A multi-lumen catheter as recited in claim 7 wherein each said tube has a length wherein said length of one said tube is different from said length of at least one other said tube and further wherein said tubes have diameters that are substantially the same size.

10. A multi-lumen catheter as recited in claim 7 wherein said first tube has an inner liner, said inner liner being bonded to said first tube with a tie layer.

11. A multi-lumen catheter as recited in claim 7 wherein each said tube is made of a thermoplastic material and wherein said thermoplastic material of one said tube is the same said thermoplastic material of at least one other said tube.

12. A multi-lumen catheter as recited in claim 7 wherein each said thermoplastic material is miscible with each other.

* * * * *